US012588895B2

(12) United States Patent
Shepard et al.

(10) Patent No.: US 12,588,895 B2
(45) Date of Patent: Mar. 31, 2026

(54) SYSTEM, METHOD, COMPUTER-ACCESSIBLE MEDIUM AND APPARATUS FOR FLEXIBLE TWO-DIMENSIONAL ULTRASOUND PHASED ARRAY

(71) Applicant: The Trustees of Columbia University in the City of New York, New York, NY (US)

(72) Inventors: Kenneth Shepard, Ossining, NY (US); Jeffrey Elloian, New York, NY (US); Tiago Costa, New York, NY (US)

(73) Assignee: The Trustees of Columbia University in the City of New York

( * ) Notice: Subject to any disclaimer, the term of this patent is extended or adjusted under 35 U.S.C. 154(b) by 543 days.

(21) Appl. No.: 16/901,289

(22) Filed: Jun. 15, 2020

(65) Prior Publication Data

US 2020/0390420 A1 Dec. 17, 2020
US 2021/0267574 A1 Sep. 2, 2021

Related U.S. Application Data

(60) Provisional application No. 62/861,054, filed on Jun. 13, 2019.

(51) Int. Cl.
A61B 8/00 (2006.01)
A61B 8/08 (2006.01)

(52) U.S. Cl.
CPC ............ A61B 8/4494 (2013.01); A61B 8/085 (2013.01); A61B 8/4236 (2013.01); A61B 2562/166 (2013.01)

(58) Field of Classification Search
CPC ... A61B 8/4236; A61B 8/4494; A61B 8/4488; A61B 8/44; H05K 1/118; H05K 1/147; H05K 1/148; B06B 1/0622
See application file for complete search history.

(56) References Cited

U.S. PATENT DOCUMENTS 9,351,706 B2 * 5/2016 Rothberg ................. A61B 8/14
11,224,895 B2 * 1/2022 Brown .................. B06B 1/0625
(Continued)

FOREIGN PATENT DOCUMENTS

EP 19162702 * 3/2019
WO 2014160964 A1 10/2014
WO WO-2017004562 A1 * 1/2017 ........... A61B 17/225

OTHER PUBLICATIONS

Zheng et al. Beam generating and sound field modeling of flexible phased arrays for inspecting complex geometric components. (Published online Dec. 14, 2019). Wave Motion, vol. 94, 102494. https://doi.org/10.1016/j.wavemoti.2019.102494. (Year: 2019).*
(Continued)

*Primary Examiner* — Anh Tuan T Nguyen
*Assistant Examiner* — Younhee Choi
(74) *Attorney, Agent, or Firm* — Hunton Andrews Kurth LLP

(57) ABSTRACT
An exemplary ultrasound (US) apparatus, can include, for example, a flexible substrate, a plurality of ultrasound transducers coupled to the flexible substrate, and an integrated circuit(s) (IC(s)) mounted on the substrate to drive and control the transducer array, where the IC(s) can be configured to control an excitation phase of the ultrasound transducers based at least in part on a shape of the flexible substrate. The ultrasound transducers can be an array of bulk piezoelectric transducers. The substrate can be a flexible printed circuit board. The IC(s) can be configured to separately control (i) a transmission of ultrasound energy from each of the transducers, (ii) a magnitude, or a (iii) phase, where the IC(s) can be configured to use the phase to focus the transmitted energy compensating for a curvature of the ultrasound apparatus.

23 Claims, 10 Drawing Sheets

(56) References Cited

U.S. PATENT DOCUMENTS

| | | |
|---|---|---|
| 2012/0289869 A1 | 11/2012 | Tyler |
| 2014/0264660 A1 | 9/2014 | Rothberg et al. |
| 2014/0303452 A1* | 10/2014 | Ghaffari .................. A61B 18/14 |
| | | 601/3 |
| 2018/0228462 A1* | 8/2018 | Maghsoudnia ...... H10N 30/802 |
| 2019/0142387 A1* | 5/2019 | Chen .................... A61B 8/5207 |
| | | 367/135 |
| 2019/0282207 A1* | 9/2019 | Chen .................... A61B 8/4272 |
| 2022/0152654 A1* | 5/2022 | Cheyns ................ B06B 1/0207 |

OTHER PUBLICATIONS

Casula et al. Control of complex components with Smart Flexible Phased Arrays. Ultrasonics (2006), vol. 44, pp. e647-e651. https://doi.org/10.1016/j.ultras.2006.05.122. (Year: 2006).*

Hiu et al. Stretchable ultrasonic transducer arrays for three-dimensional imaging on complex surfaces. Science Advances (2018), 4: eaar3979. https://doi.org/10.1126/sciadv.aar3979. (Year: 2018).*

Pashaei et al. Conformal Ultrasound Transducer Array for Image-Guided Neural Therapy. 2018 IEEE Biomedical Circuits and Systems Conference (BioCAS). Published Online Dec. 23, 2018. https://doi.org/10.1109/BIOCAS.2018.8584727. (Year: 2018).*

Tumsys et al. (2014). The Focusing of the Ultrasonic Phased Array in the Case of Non-contact NDE Methods. Elektronika Ir Elektrotechnika, 20(3), 44-47. https://doi.org/10.5755/j01.eee.20.3.3638. (Year: 2014).*

Yang et al. (2013). A flexible piezoelectric micromachined ultrasound transducer. RSC Advances. 3. 24900. Doi: 10.1039/c3ra44619k.) (Year: 2013).*

Dagdeviren D. et al., "Flexible piezoelectric devices for gastrointestinal motility sensing" Nature Biomedical Engineering, vol. 1, pp. 807-817, Oct. 2017.

Gerardo CD et al., "Fabrication and testing of polymer-based capacitive micromachined ultrasound transducers for medical imaging" Nature Microsystems and Nanoengineering, vol. 4 / Issue 19, Aug. 2018.

Davidsen RE, Smith SW, "Two-dimensional arrays for medical ultrasound using multilayer flexible circuit Interconnection" IEEE, vol. 45 / Issue 2, Apr. 2011.

Chen C, et al. "A front-end ASIC with receive sub-array beamforming integrated with a 32×32 PZT matrix transducer for 3-D transesophageal echocardiography" IEEE, Jun. 2016.

Tang G, et al. "Fabrication and analysis of high-performance piezoelectric MEMS generators" Journal of Micromechanics and Microengineering, vol. 22 / Issue 6, May 2012.

Wang C,net al. "Monitoring of the central blood pressure waveform via a conformal ultrasonic device" Nature Biomedical Engineering, vol. 4 / Issue 19, Aug. 2018.

Shi C, Costa T, Elloian J, Shepard KL. Monolithic Integration of Micron-scale Piezoelectric Materials with CMOS for Biomedical Applications. IEEE. Jan. 2019.

Fleischer DA, Shekar S, Dai S, Field RM, Lary J, Rosenstein JK, Shepard KL. CMOS-Integrated Low-Noise Junction Field-Effect Transistors for Bioelectronic Applications. IEEE. Jul. 2018; 39(7): pp. 931-934.

Park JS, et al., "Acoustic and electromechanical properties of 1-3 PZT composites for ultrasonic transducer arrays fabricated by sacrificial micro PMMA mold" Sensors and Actuators A: Physical, vol. 8 / Issue 1-3, Jun. 2003.

A Dissertation in Electrical Engineering by Insoo Kim "Fully Integrated Cmos Ultrasound Transceiver Chip for High-Frequency High-Resolution Ultrasonic Imaging Systems," The Pennsylvania State University The Graduate School College of Engineering (Dec. 2009).

Notice of Allowance for U.S. Appl. No. 15/858,247 mailed on Nov. 23, 2023.

Corrected Notice of Allowability for U.S. Appl. No. 15/858,247 mailed on Dec. 2, 2023.

D.M.J. Cowell et al. "Quinary excitation method excit for pulse compression ultrasound measurements," Ultrasonics, vol. 48, Issue 2, Apr. 2008, pp. 98-108.

* cited by examiner

205

210

205
Piezoelectric
Elements

210
Flex PCB

Thinned
Master ICs
220

Thinned
Slave ICs
215

Figure 6A
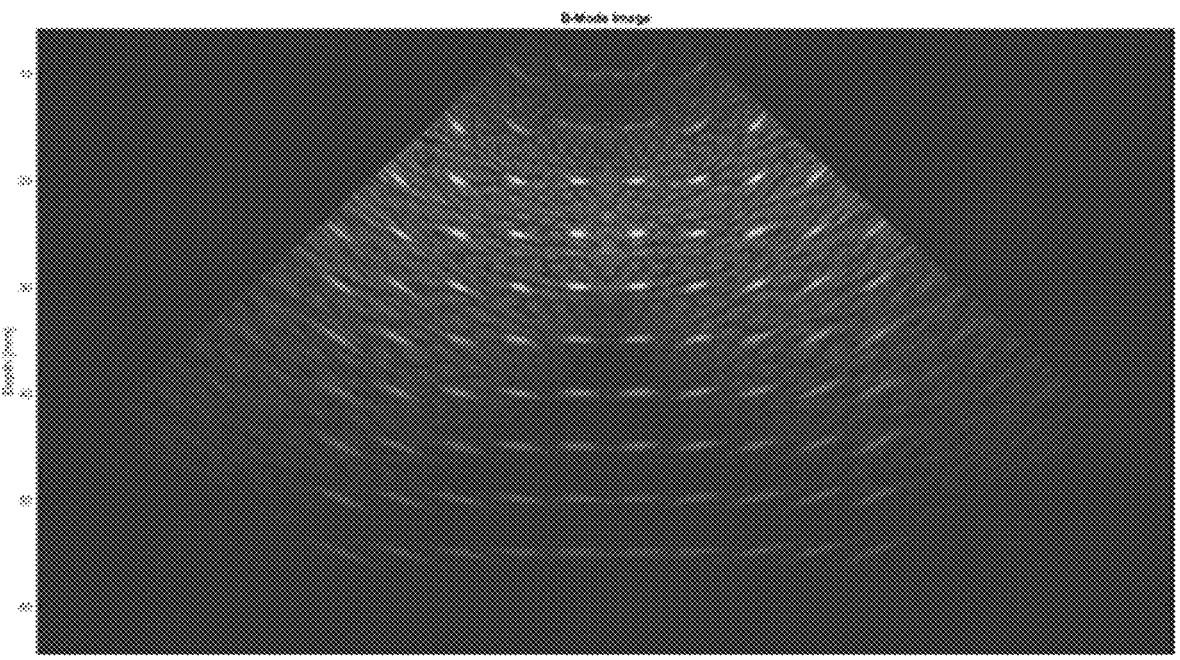
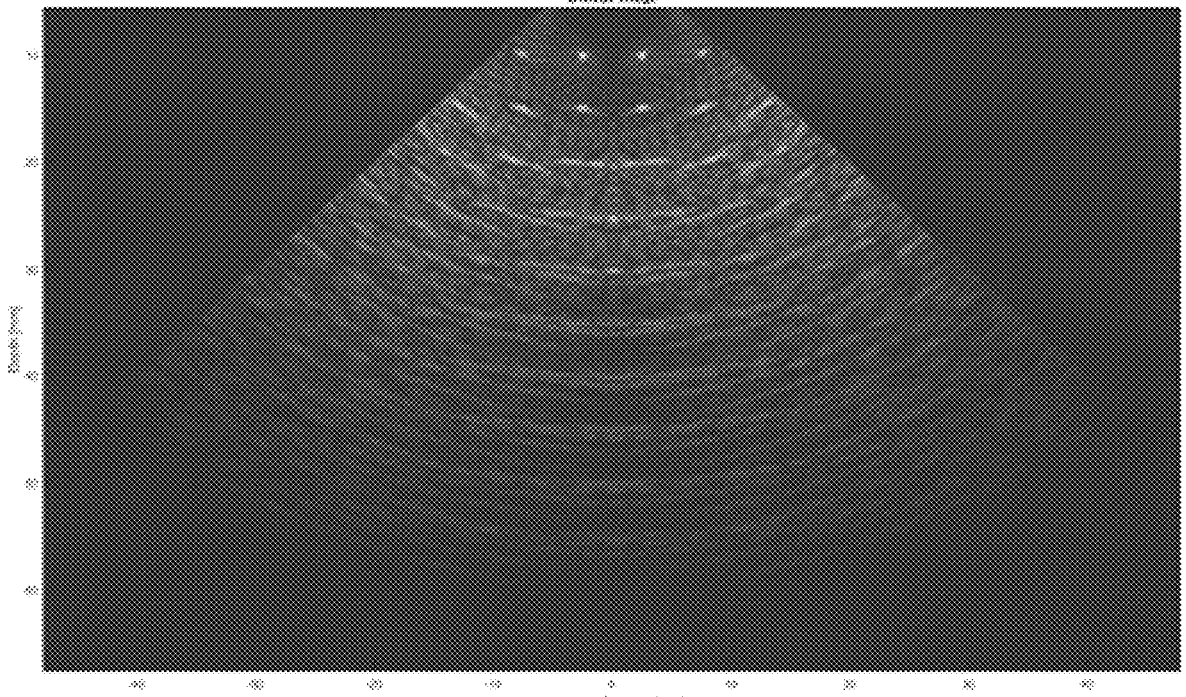
Figure 6B

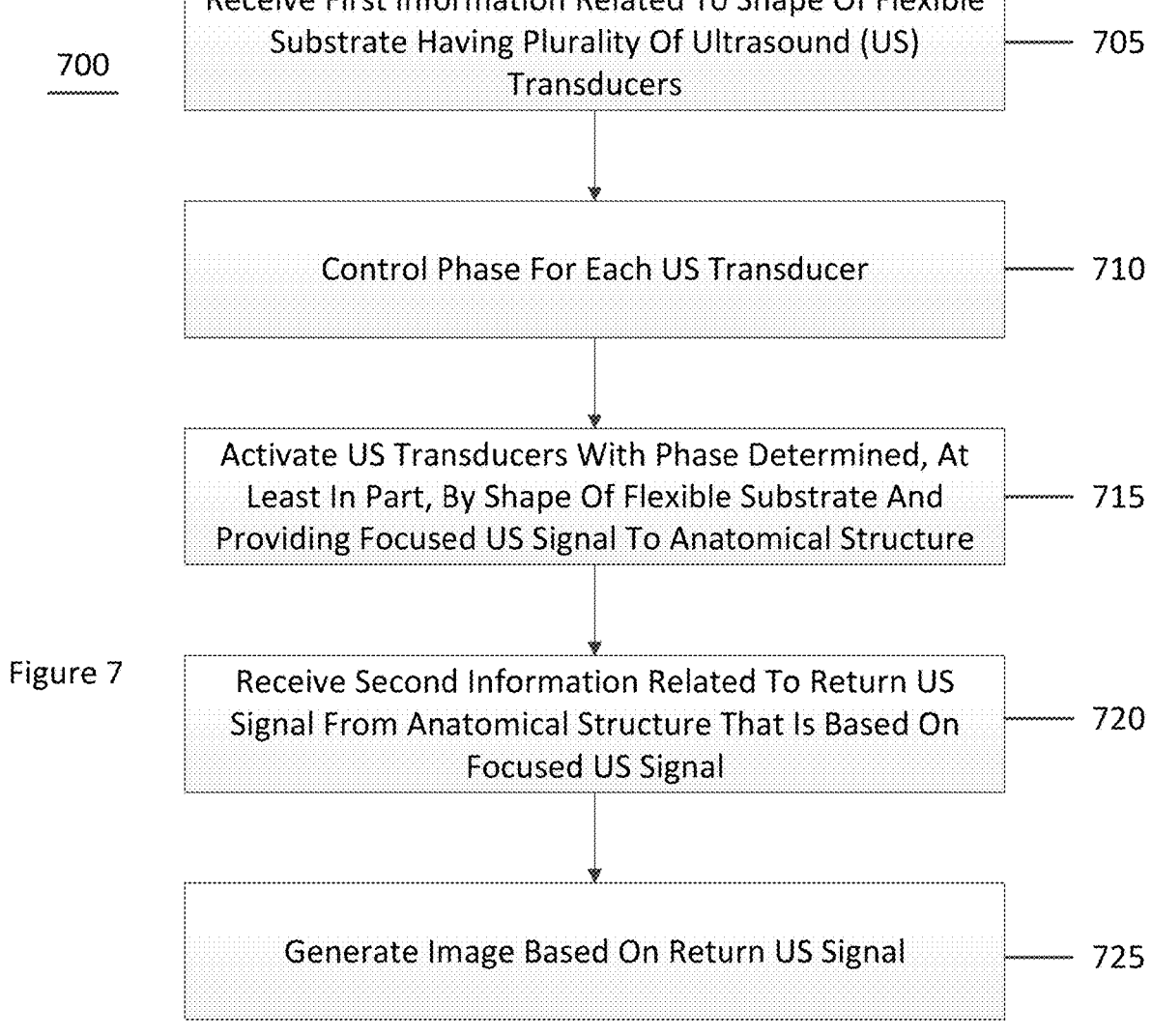

Receive First Information Related To Shape Of Flexible Substrate Having Plurality Of Ultrasound (US) Transducers — 705

Control Phase For Each US Transducer — 710

Activate US Transducers With Phase Determined, At Least In Part, By Shape Of Flexible Substrate And Providing Focused US Signal To Anatomical Structure — 715

Receive Second Information Related To Return US Signal From Anatomical Structure That Is Based On Focused US Signal — 720

Generate Image Based On Return US Signal — 725

SYSTEM, METHOD, COMPUTER-ACCESSIBLE MEDIUM AND APPARATUS FOR FLEXIBLE TWO-DIMENSIONAL ULTRASOUND PHASED ARRAY

CROSS-REFERENCE TO RELATED APPLICATION(S)

This application relates to and claims priority from U.S. Patent Application No. 62/861,054, filed on Jun. 13, 2019, the entire disclosure of which is incorporated herein by reference.

STATEMENT REGARDING FEDERALLY SPONSORED RESEARCH

This invention was made with government support under Grant No. HR0011-15-2-0054, awarded by the Defense Advanced Research Projects Agency. The government has certain rights in the invention.

FIELD OF THE DISCLOSURE

The present disclosure relates generally to ultrasound, and more specifically, to exemplary embodiments of an exemplary system, method, computer-accessible medium, and apparatus for providing and/or utilizing a flexible two-dimensional ultrasound phased array.

BACKGROUND INFORMATION

Modern diagnostic medicine is trending towards decreasing invasiveness of medical examinations to improve patient comfort, without compromising the quality of the diagnosis. Medical professionals need an accurate procedure for using ultrasound to image patients and to adapt to different body geometries. For example, an endotracheal tube insertion is a difficult precision operation that is currently conducted with ad-hoc application of traditional ultrasonic probes as opposed to purpose-built devices. The trachea is naturally a curved surface on the human body, and flat transducers suffer reduced image quality from the inherent air gap. Moreover, the medical professional must manually hold the probe during the insertion process, risking serious injury if the tube is misplaced.

In addition, extended term patient monitoring can be vital for intensive care units. This is especially the case for minors, who, with smaller external surfaces, can greatly benefit from a flexible patch. While diagnostic ultrasound procedures have been developed for measuring various vitals, such procedures generally rely on static probes, which are manually manipulated. It would be impractical to mount these probes for extended periods of time. An ultrasound patch with a patch form factor can facilitate a safer and more comfortable monitoring of the patient.

Although commercial curved phased arrays are available for clinical use, these typically have a fixed radius of curvature. These curved phased arrays do not necessarily comfortably fit all body types, and their use is limited to a region of the body of that approximate shape. Moreover, the phasing of the elements needs to be adjusted to correspond with the given curvature or the image will suffer distortion. Thus, it may be beneficial to provide an exemplary system, method, computer-accessible medium, and apparatus for flexible two-dimensional ultrasound phased array, which can overcome at least some of the deficiencies, described herein above.

SUMMARY OF EXEMPLARY EMBODIMENTS

An exemplary ultrasound ("US") apparatus can include, for example, a flexible substrate, a plurality of ultrasound transducers disposed on the flexible substrate, and an integrated circuit(s) ("IC" (s)) mounted on the substrate to drive and control the transducer array, where the IC(s) can be configured to control an excitation phase of the ultrasound transducers based at least in part on a shape of the flexible substrate. For example, the IC(s) can include at least two ICs, whereas a first IC of the ICs can be configured to drive and/or control the ultrasound transducers, and a second IC of the ICs can be configured to control the first IC. The ultrasound transducers can be an array of bulk piezoelectric transducers. The substrate can be a flexible printed circuit board. The IC(s) can be configured to separately control (i) a transmission of ultrasound energy from each of the transducers, (ii) a magnitude, or a (iii) phase, where the IC(s) can be configured to use the phase to focus the transmitted energy compensating for a curvature of the ultrasound apparatus. The IC(s) can be configured to receive and detect back-reflected ultrasound energy from elements of the transducer array to form an image. The IC(s) can include a plurality of ICs, where each of the ICs can be configured to control a phase of a subset of the ultrasound transducers. The IC(s) can be a complementary-metal-oxide-semiconductor ("CMOS") chip.

In certain exemplary embodiments of the present disclosure, the IC(s) can be a thinned and flexible CMOS chip. The ultrasound transducers can be mounted on the thinned and flexible CMOS chip. The ultrasound transducers can include, e.g., (i) a first transducer array(s) and (ii) a second transducer array(s), the IC(s) can include (i) a first slave IC(s), (ii) a second slave IC(s), and (iii) a master IC(s), the first transducer array(s) can be mounted on the first slave IC(s), the second transducer array(s) can be mounted on the second slave IC(s), and the first slave IC(s) and the second slave IC(s) can be controlled by the master IC(s). The first slave IC(s) can control the excitation phase of each transducer in the first transducer array(s) and (ii) the second slave IC(s) can control the excitation phase of each transducer in the second transducer array(s).

In some exemplary embodiments of the present disclosure, a computer arrangement(S) can be included, which can be configured to receive ultrasound imaging information from the IC(s), and generate an image(s) based on the ultrasound imaging information. The ultrasound apparatus can be configured to be attached to a patient(s).

Additionally or alternatively, an exemplary ultrasound (US) apparatus can be provided, which can include, for example, a flexible printed circuit board (PCB), a plurality of slave complementary-metal-oxide-semiconductor (CMOS) chips disposed on the flexible PCB, a plurality of ultrasound transducer arrays, where each of the ultrasound transducer arrays can be mounted on, and controlled by, one of the slave CMOS chips, and a master CMOS chip(s) configured to control the slave CMOS chips. The slave CMOS chips can be thinned and flexible slave CMOS chips and the master CMOS chip(s) can be a thin and flexible master CMOS chip(s). The ultrasound transducer arrays can include a plurality of piezoelectric transducers. A computer arrangement(S) can be included and/or provided, which can be configured to (i) receive ultrasound imaging information from the master CMOS chip(S), and (ii) generate an image (S) based on the ultrasound imaging information. The ultrasound apparatus can be configured to be attached to a patient(s).

Additionally, an exemplary system, method and computer-accessible medium for generating an image of an anatomical(s) structure according to an exemplary embodiment of the present disclosure can be provided, which can include, for example, a receipt of first information related to a shape of a flexible substrate having a plurality of ultrasound ("US") transducers, a control of a phase for each of the ultrasound transducers, activating the ultrasound transducers with a phase determined, at least in part, by the shape of the flexible substrate, providing a focused ultrasound signal to the anatomical structure(s), a receipt of second information related to a return ultrasound signal from the anatomical structure(s) that can be based on the focused ultrasound signal, and a generation of the image based on the return ultrasound signal.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 6A is an exemplary diagram illustrating simulation results showing the effect of a 2 cm radius of curvature on a 16×16 element array using curvature adjusted phasing according to an exemplary embodiment of the present disclosure;

FIG. 6B is an exemplary diagram illustrating simulation results showing the effect of a 2 cm radius of curvature on a 16×16 element array using standard phasing according to an exemplary embodiment of the present disclosure;

FIG. 7 is an exemplary flow diagram of a method for generating an image of an anatomical structure according to an exemplary embodiment of the present disclosure.

Figure 1:
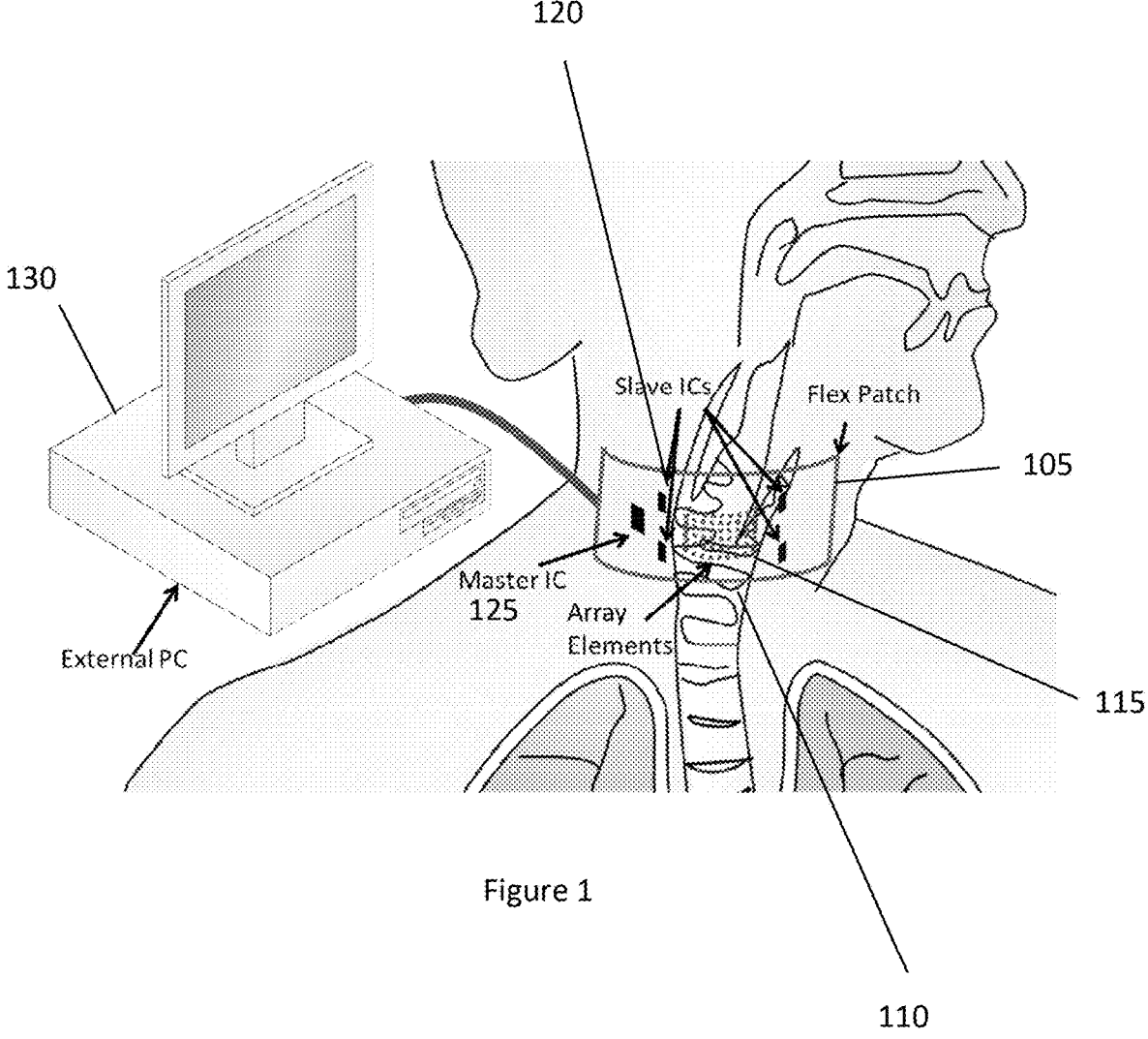
FIG. 1 is an exemplary diagram of an exemplary flexible ultrasound patch array mounted to the throat of a patient according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

A flexible ultrasound phased array patch and exemplary methods for fabricating thereof are described herein. For example, the flexible ultrasound phased array can include a flexible printed circuit board ("flex-PCB") connected to an application-specific integrated circuit ("ASIC") provided for computation and control. This ASIC, which can be or can include a complementary-metal-oxide-semiconductor ("CMOS") integrated circuit ("IC") chip, can also be thinned or otherwise reduced in width to make it flexible. The exemplary PCB can be or can include a polyimide-based flex-PCB, which can act as a substrate for multiple independent ultrasound transducers (e.g., 256 independent transducers). The transducers can be piezoelectric transducers, and/or other suitable transducers can be used. Using the signals passed from the dynamically controlled external circuitry, each transducer can transmit and receive ultrasound signals.

The exemplary ultrasound phased array can be used for B-mode imaging, and the exemplary device can be electronically configured to operate in different modes. The excitation phased can be adjusted by the controller ASIC to configure the focus location and scanning characteristics dynamically during use. The phasing can be corrected to adjust for the new positions of the transducer elements as the flexible array can be curved to conform to a target. The exemplary non-invasive patch array can be mounted, attached or otherwise connected to the subject directly, effectively making it wearable. This can facilitate comfortable long-term measurements that can otherwise be impractical with traditional probes.

The exemplary embodiments of the present disclosure can also provide filling of the kerfs formed between the ultrasound transducer pillars with a biocompatible epoxy.

An exemplary non-invasive flexible 2D ultrasound phased array patch and exemplary methods of fabricating thereof are also described herein. For example, the phased array can use B-mode ultrasound imaging by employing pulsed ultrasound transmission that can produce two-dimensional ("2D") and/or three-dimensional ("3D") imaging of a region of interest. The phases of individual elements can be controlled by external signals to the elements such that the delays can facilitate the ultrasound pulse to arrive at the user-defined focus at the same time, maximizing the power and resolution in this region of interest. The same or similar phasing can be applied in the receive mode to constructively add the contributions from all elements to maximize the signal-to-noise ratio. The exemplary focus can dynamically be changed for each pulse, facilitating a sweep of multiple scans to construct an image The flex-PCB can function as both the substrate for the transducers as well as the patch itself. The flex-PCB can be of any suitable size depending on the location the patch is to be placed. For example, the flexible-PCB can have the size of approximately 50 mm by approximately 100 mm (plus or minus about 10%) with a thickness of approximately 200 μm (plus or minus about 10%). This exemplary configuration can be connected with the external ASIC circuitry for rapid interchangeability of patches. Such exemplary configuration can facilitate the flex-PCB to be replaced and hot-swapped as needed depending on the area to be imaged. For example, the area of the connector can be intentionally stiffened with a FR4 backing, which can be distanced enough away to avoid impeding the flexibility of the remainder of the array. Alternately, the ASIC can be mounted on the flex-PCB directly.

FIG. 1 shows an exemplary diagram of an exemplary flexible ultrasound patch array 105 mounted to the throat 110 of a patient according to an exemplary embodiment of the present disclosure. Any suitable biocompatible temporary adhesive can be used to hold or otherwise maintain attached patch 105 to the surface of the skin so as to facilitate array elements 115 to make direct contact with the skin. Array elements 115 can be controlled using one or more slave ICs 120, which can be controlled by one or more master ICs 125. Patch 105 can be in communication with an external computing device 130, which can include a computer, a tablet, a mobile device, or any other suitable computing device that can interface with patch 105. Additionally, various wired or wireless communication mediums can be used to connect patch 105 to computing device 130. The flexibility of array 115 can facilitate the exemplary patch 105 to conform to the human body, and provide accurate imaging in areas that mechanically difficult to use traditional rigid probes.

Exemplary piezoelectric transducer options can be, or can include, polyvinylidene fluoride or polyvinylidene difluoride ("PVDF"), selected for its excellent matching to human tissue and superb flexibility in comparison to other piezoelectric devices. To achieve greater power, the same array can also be used with alternative transducer materials such as lead zirconate titanate ("PZT"), lead magnesium niobate-lead titanate ("PMN-PT") crystals, or a piezocomposite. While providing a greater electromechanical coupling coefficient than PVDF, the acoustic mismatch can be worse, which can benefit from the use of a matching layer. While the same operating principles hold for all of the aforementioned piezoelectric materials, the fabrication steps can be modified to accommodate the specific material used.

The exemplary array design can be a two-dimensional array including any suitable number of array elements depending on the size and shape to be achieved. For example, the array can include 16×16 elements with a pitch of 1 mm (plus or minus about 10%). The individual elements can be of any suitable size (e.g., about 425 μm plus or minus about 10%). Other pitches, element sizes, and element counts can certainly be employed in accordance with the exemplary embodiments of the present disclosure. In such exemplary embodiment and for PVDF elements operating in the piezoelectric thickness mode of operation, each element can be approximate 110 μm tall (plus or minus about 10%), providing a quarter-wavelength resonance of 3.5 MHz (plus or minus about 10%). The functional bandwidth of the transducers can be from about 1 MHz (plus or minus about 10%) to approximately 8 MHz (plus or minus about 10%). At 3.5 MHz and a depth of 2 cm, the lateral resolution can be about 1.1 mm (plus or minus about 10%) and the axial resolution can be approximately 210 μm (plus or minus about 10%), providing an image sufficient to determine large obstructions.

Figure 2A:
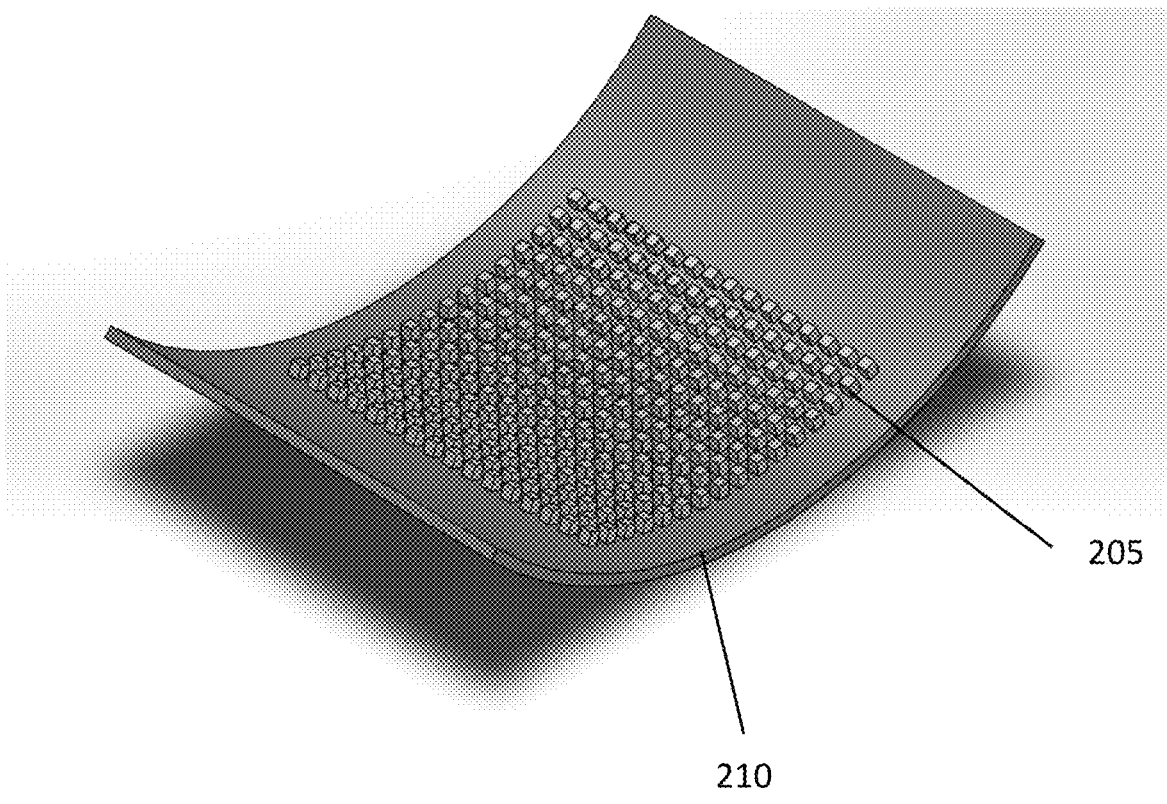
FIG. 2A is an exemplary image of piezoelectric elements mounted to a flexible printed circuit board according to an exemplary embodiment of the present disclosure.

Other exemplary materials can be used that can provide the same axial resolution, and with greater pressure, quality factor, and thickness. For example, piezo elements made of PMN-PT at about 3.5 MHz (plus or minus about 10%) may need to be 658 μm thick, and can have bandwidth from about 3.47 MHz (plus or minus about 10%) to about 3.53 MHz (plus or minus about 10%). The exemplary device can be flexible over the entire active area of the array, which can be approximately 15.45 mm×15.45 mm (plus or minus about 10%), regardless of the material used for the transducers. The processing for manufacturing this array can facilitate a radius of curvature of at least 2 cm (plus or minus about 10%) without failure, as illustrated in FIG. 2A. For example, FIG. 2A shows an exemplary image of piezoelectric elements 205 mounted to a flexible printed circuit board 210 according to an exemplary embodiment of the present disclosure.

Figure 2B:
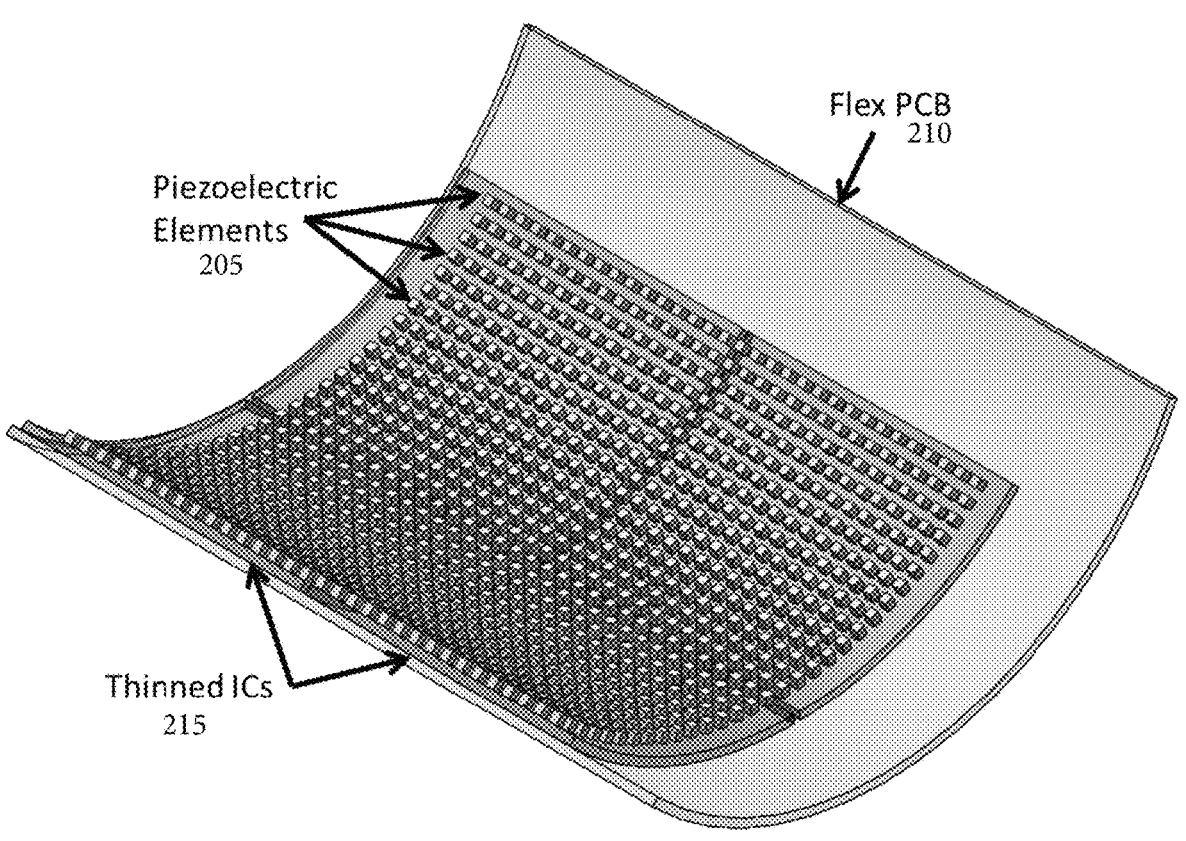
FIG. 2B is an exemplary image of piezoelectric elements mounted on a thinned CMOS chip according to an exemplary embodiment of the present disclosure.

FIG. 2B shows an exemplary image of piezoelectric elements 205 (as illustrated in FIG. 2A) mounted on one or more thinned ICs 215 (e.g., which can be CMOS chips) according to an exemplary embodiment of the present disclosure. Thinned ICs 215 can include circuitry to directly control the phasing of the individual elements (e.g., the individual piezoelectric elements). The thinned ICs facilitate greater flexibility of the exemplary apparatus, while also facilitating the routing length to the elements to remain short because of their close proximity. Thinning the ICs can be performed a post-processing procedure that can be performed, e.g., by mechanical grinding, followed by polishing, to remove a large part of the non-active bulk of the IC.

Figure 2C:
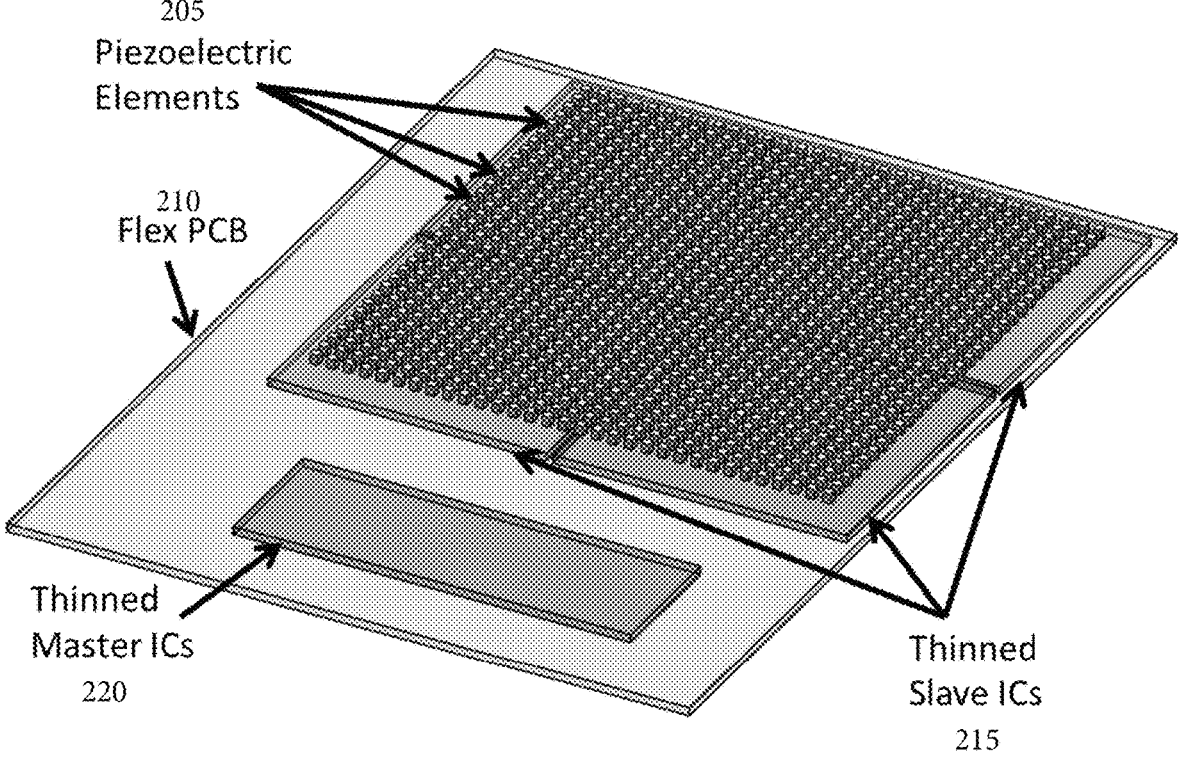
FIG. 2C is an exemplary image of piezoelectric elements mounted on tiled and thinned slave integrated circuits according to an exemplary embodiment of the present disclosure.

FIG. 2C shows an exemplary image of piezeoelectric elements 205 (as illustrated in FIGS. 2A and 2B) mounted on tiled and thinned slave integrated circuits according to an exemplary embodiment of the present disclosure. As shown in FIG. 2C, flexible PCB 210 can include multiple tiled ICs 215 (e.g., slave ICs) controlled by a master IC 220. For example, each slave IC 215 can receive instructions (e.g., including phasing codes) from master IC 220, that can also be mounted on flexible PCB 210. Each slave IC 215 can control a corresponding sub-set of piezeoelectric elements 205, for example, using a clock to produce the relevant delayed signals for each piezoelectric element 205. The same delay, or a different delay, can then be used for summing the received signals for image reconstruction. According to an exemplary embodiment of the present disclosure, each slave IC 215 may only communicate with its subset of piezoelectric elements 205 and its associated the master IC 220. This can reduce the amount of required or preferred inter-array routing, facilitating scalability to large array sizes. The reconstructed image data from each subarray can be independent from neighboring slave ICs, which can be communicated to the master IC. As shown in FIG. 2C, for example, a single master IC can be used to control multiple slave ICs. However, multiple master ICs can be used, each controlling a group of slave ICs.

Figure 3:
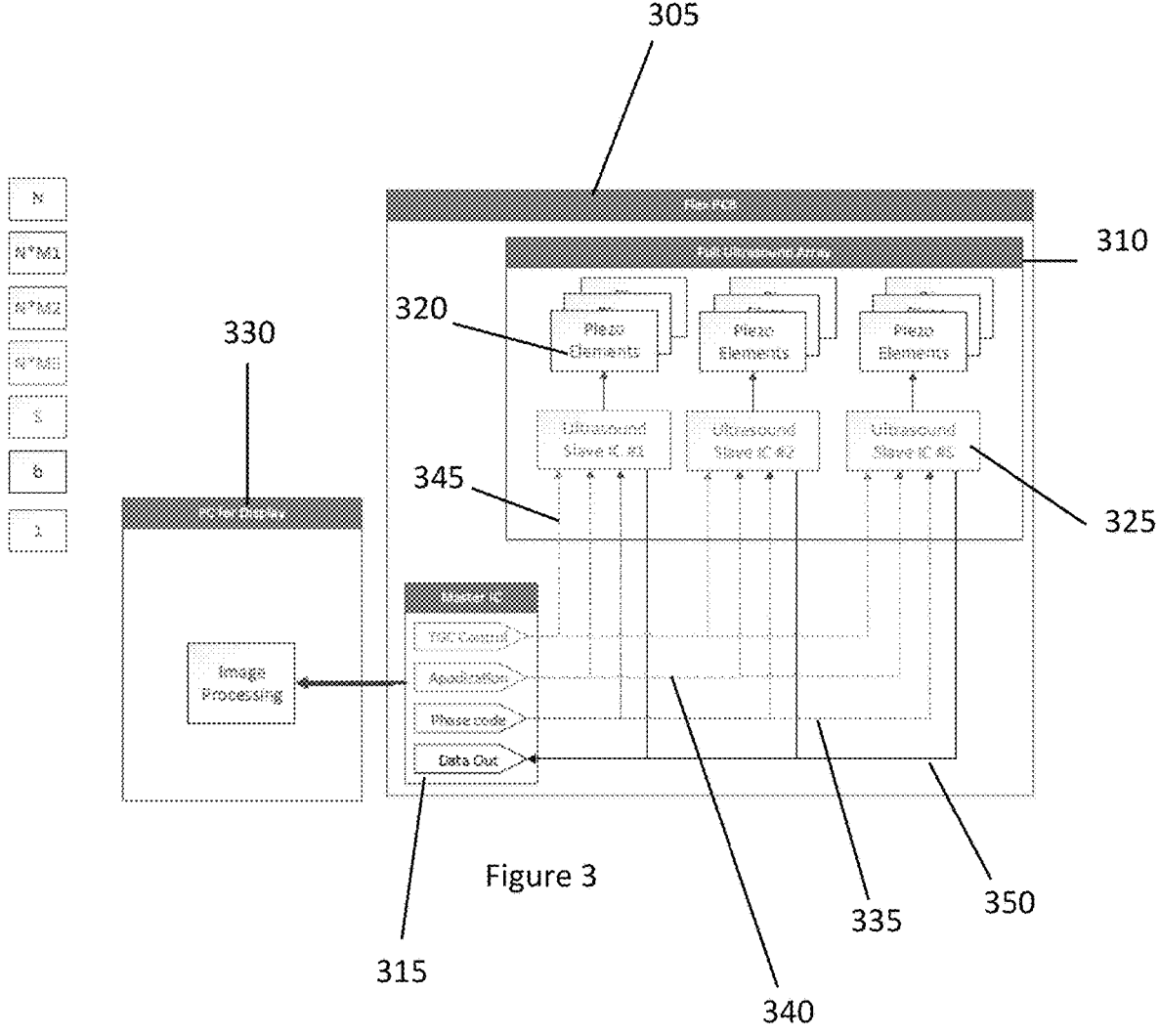
FIG. 3 is an exemplary diagram illustrating the data flow of the exemplary ultrasound patch according to an exemplary embodiment of the present disclosure.

FIG. 3 shows an exemplary diagram illustrating the data flow of the exemplary ultrasound patch according to an exemplary embodiment of the present disclosure. For example, as shown in FIG. 3, a flexible PCB 305 can have a full ultrasound array 310 and a master IC 315 integrated therein. Full ultrasound array 310 can have a plurality of piezoelectric elements 320 and a plurality of ultrasound slave ICs 325 integrated therein. As the ASIC can already have the phase code for each element, it can shift each set of registers by the corresponding number of time samples. This can be the digital equivalent of adding a delay. With the phasing having been compensated for, the data from all elements at each individual time can be summed to produce a single digital time stream. Such bit stream can then be serially transmitted to the master IC 315, which can be, e.g., the sum all of the streams from each of its corresponding slave ICs 325. The phase can be taken into account by each slave IC 325. This final bit stream can then be transmitted to an external PC controller 330 to form a single line in B-mode image or for additional, optional signal processing. As illustrated in FIG. 3, each line and block can illustrate the respective widths. For example, N can be the number of elements, K can be the number of analog-to-digital converters ("ADCs") that the bit streams can be multiplexed into, and b can be the number of output bits of the data stream. M1, M2, and M3 represent the number of control bits for phasing, apodization, and time gain compensation ("TGC") control, respectively. Line 335 represents N*M1, line 340 represents N*M2, line 345 represents N*M3, and line 350 represents the output b.

Figure 4:
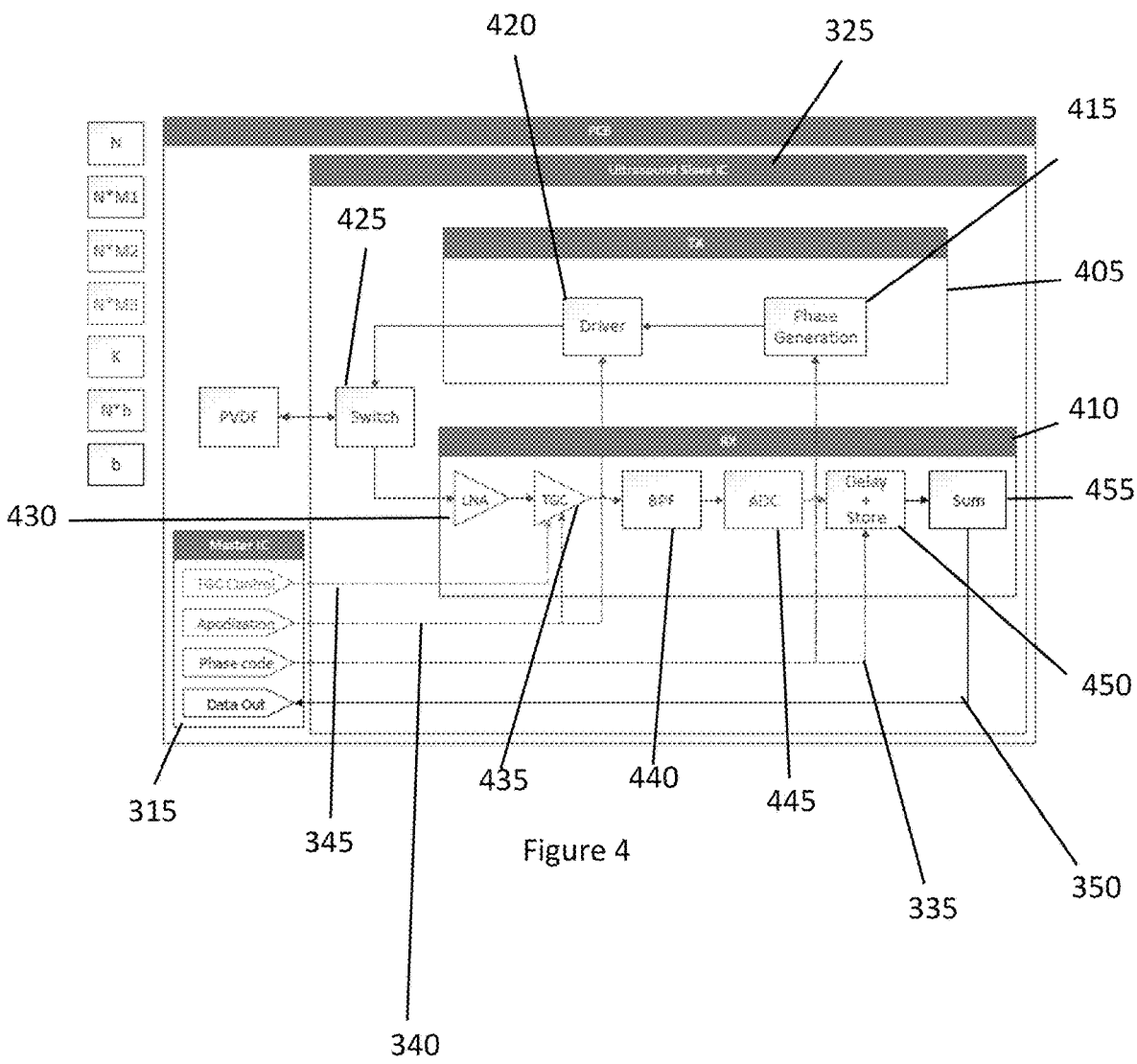
FIG. 4 is an exemplary diagram of a slave integrated circuit showing the widths of each data path according to an exemplary embodiment of the present disclosure.

The analog front end ("AFE") and ADC can be performed by an ASIC that can be mounted directly to the board. This procedure can reduce or minimize the amount of routing needed directly on the board, providing flexibility and facilitating greater density, while simultaneously utilizing fewer external input/output ("I/O") lines. The exemplary ASIC can provide a single line for each transducer, a clock, phasing information for each element, and control signals. As the phasing can be known a priori to transmission, and the data can linearly be phased and added independent of neighboring elements, it can be possible to further reduce routing by grouping elements and setting their phase together. To facilitate this, separate slave ICs can obtain phasing from a master IC, where each slave can coordinate with a fixed sub-section of the full array, as shown in FIG. 4. For example, FIG. 4 illustrates an exemplary diagram of a slave IC 325 illustrating the widths of each data path according to an exemplary embodiment of the present disclosure. Each slave IC 325 only needs the phasing data for each element of its own section. Likewise, the output can be simplified by having a single data-line out as opposed to a single one for each element. The received signals at each slave can be delayed and summed locally (e.g., the phase data can already be available), and the master IC 315 may only need to sum the result from each slave.

The exemplary circuit can include separate transmit and receive paths (e.g., transmit path 405 and receive path 410). To transmit, a digital phase code (e.g., phase generation 415) can be sent to the delay circuit, which can generate, for example, a delayed bi-polar 100V square pulse to the corresponding element via a stacked transistor driving circuit (e.g., driver 420). These pulses can occur independently for each element. After each transmit event, an integrated switch 425 within the IC can enable or facilitate the receive path 410. Paths 405 and 410 may never be on simultaneously in order to prevent damage to the circuit. The receive path 410 can begin with a low noise amplifier ("LNA") 430 with a gain a suitable gain (e.g., a gain of 26 dB plus or minus about 10%), and a bandwidth of 10 MHz (plus or minus about 10%). The signal can then pass from an LNA, through TGC 435, to a band pass filter ("BPF") 440 with a suitable cutoff (e.g., a 1 MHz cutoff plus or minus about 10%) before being sampled by an ADC 445. The BPF may be replaced by a high pass filter ("HPF"); utilizing the LNA to filter out lower frequencies such that the combination of the two filters can function similar to a BPF. The new digital data can be delayed and stored (e.g., element 450) and summed internally (e.g., element 455) to master IC 315 before being serialized to an output to an external controller.

The digital beamforming can be implanted with a series of exemplary counter circuits having, for example, a 32 MHz clock (plus or minus about 10%), facilitating a phase resolution of about 31 ns (plus or minus about 10%). An exemplary 8-bit counter can facilitate a max delay between elements of about 8 us. The delay value for each element can be, for example, an 11-bit value that can be decoded and held in a register. For example, 8 of the 11 bits can be used to define the delay value for the element in the counter by loading it. 2 of the 11 bits can be used to determine the length of the pulse in cycles. This can facilitate a variable number of pulses from 1 to 4 cycles. The remaining bit can be used for apodization, which can mask individual elements to turn them off. This pulse train can then be sent to an H-bridge driving circuit to convert the delayed pulses from 1.8V to +/−180V bi-polar pulses, which can be fed directly to the transducers. The loaded described control bits may only be read when the fire signal from the master can be sent. This can facilitate a synchronization across multiple slave ICs. The transit path circuitry can be replicated for each individual element.

Each element can also receive an independent receive path in the slave ASIC. After the transmit event can be complete, a signal can be sent to the receive path to disconnect the H-bridge and the entire transmit circuit. The input can be received and fed directly into a LNA from the transducer to minimize noise. The close proximity of the IC to the individual transducers can assist with combating the effect of the low input capacitance of each element. It may not be practical for a 150 fF input capacitance to then drive a cable of several pF. After the LNA, each element can be subjected to a BPF to eliminate low frequency noise and isolate the frequency band of the expected echo. Each signal can be sampled by an ADC operating at 32 MHz (plus or minus about 10%) to convert each signal into a digital data stream.

The fabrication process to construct the transducers can be dependent on the piezoelectric material used. PVDF, with a Curie temperature of 195 C, can be processed at or below 70C to maintain its piezoelectric properties. Both PZT and PMN-PT have Curie temperatures above levels used in traditional photolithography and bonding procedures, simplifying fabrication and improving yield.

The pads on the flex-PCB can be selected to electroless nickel immersion gold ("ENIG") facilitating sufficiently thick metal traces (e.g., in excess of 5 um) to survive laser processing, as well as a gold finish to minimize capacitance introduced from an interposing layer of oxide on the transducer pads. The ASIC can be wirebonded to the flex PCB after processing the pillars using gold-gold wirebonding at 80 C.

For adhesion, a negatively photopaternable epoxy SU-8 can be used. The traditional bonding processes can include curing the SU-8 in the desired pattern before bonding using force and heating the SU-8 above its glass transition temperature near 200 C. Instead, this device uses an exemplary procedure for bonding during the cross-linking process. The SU-8 resist can first be spin cast into a 5 μm layer across the surface of the substrate, followed by a traditional soft bake at 95 C to remove excess solvent. The flex board can then be selectively exposed under a mask aligner to activate the resist. Only the metal pads where PVDF can ultimately remain exposed. Instead of performing a traditional post-exposure bake ("PEB"), a 2 cm×2 cm piece of PVDF can be placed on top of the array of pads. A glass side with a protective layer of hard baked Poly(methyl methacrylate) ("PMMA") can be placed on top this stack to provide uniform pressure. The side of the glass with the PMMA can be face down towards the PVDF, which can be dissolved in acetone if excess SU-8 escapes the side and makes contact with the glass. 688 kPa of pressure can be applied to the top of this stack while heating it from the bottom at 70 C for 30 minutes. This can facilitate the bond to form during the polymerization of the SU-8 as opposed to standard reflow procedures. At the end of this process, there can be 5 um pillars of cured SU-8 supporting the entire 2 cm×2 cm sheet of PVDF.

To expose these pillars, a 193 nm excimer laser was used. The deep UV wavelength can be well absorbed by PVDF facilitating the clean patterning of individual pillars. Rastering the entire region between pads can take a prohibitively long time. Instead, each element can be traced by the laser, which can focus down as it cuts. This exemplary process can result in each PVDF pillar standing isolated on a platform of SU-8 on top of each pad. As the remaining PVDF may not be held on by any SU-8, it can easily be remove with tweezers or placing the device in a solvent.

The generation of these pillars on PZT and PMN-PT can be different, due to the ceramic nature of these materials. Gold pads, where there pillars can be located, can be patterned on both sides of the PZT or PMN-PT to define metal contacts. The piezomaterial can then be tacked to an anisotropic conductive film ("ACF") before being diced in a dicing saw. Initially, the pillars may not be completely exposed, but can be cut 80% of the way through. The previously patterned gold pads can then be used to align the material over the gold pads of the PVDF and bond using the ACF at 150 C and 2.16 MPa of force. The can ACF facilitate electrical contact vertically between the pads on the PCB and the piezoelectric pillars, without shorting horizontally across the array. An exemplary advantage in comparison to the patternable SU-8 method with PVDF can be that this can minimize parasitic capacitance by eliminating the non-conductive gap between the piezo and the pad. Dicing can then be used to fully separate each pillar. The heat and tearing motion of these two processes preclude their use with PVDF.

The kerf between pillars, regardless of the material, can then be filled with a flexible biocompatible epoxy and facilitated to cure overnight. Sputter deposition can then be used to deposit a 10 nm layer of Chromium followed by 600 nm layer of Copper to connect the top of all of the pillars to a ground pad. Each element can act as a capacitor with the top plate grounded and the bottom plate connected to each signal pad.

Passivation can then be completed with a layer of parylene C, which can function as a matching layer for the PVDF. When working with PMN-PT or PZT, an additional procedure of generating a separate matching layer can be inserted before passivation. For example, a layer of 301-2 epoxy can be mixed with Tungsten particles to reach the desirable acoustic impedance. The epoxy can then be lapped to a $\lambda/4$ thickness via mechanical milling before dicing into pillars on a dicing saw and bonding to the surface of the piezoelectric pillars. Passivation can then be performed with parylene C in the same manner as can be performed for PVDF.

Figures 5A, 5B:
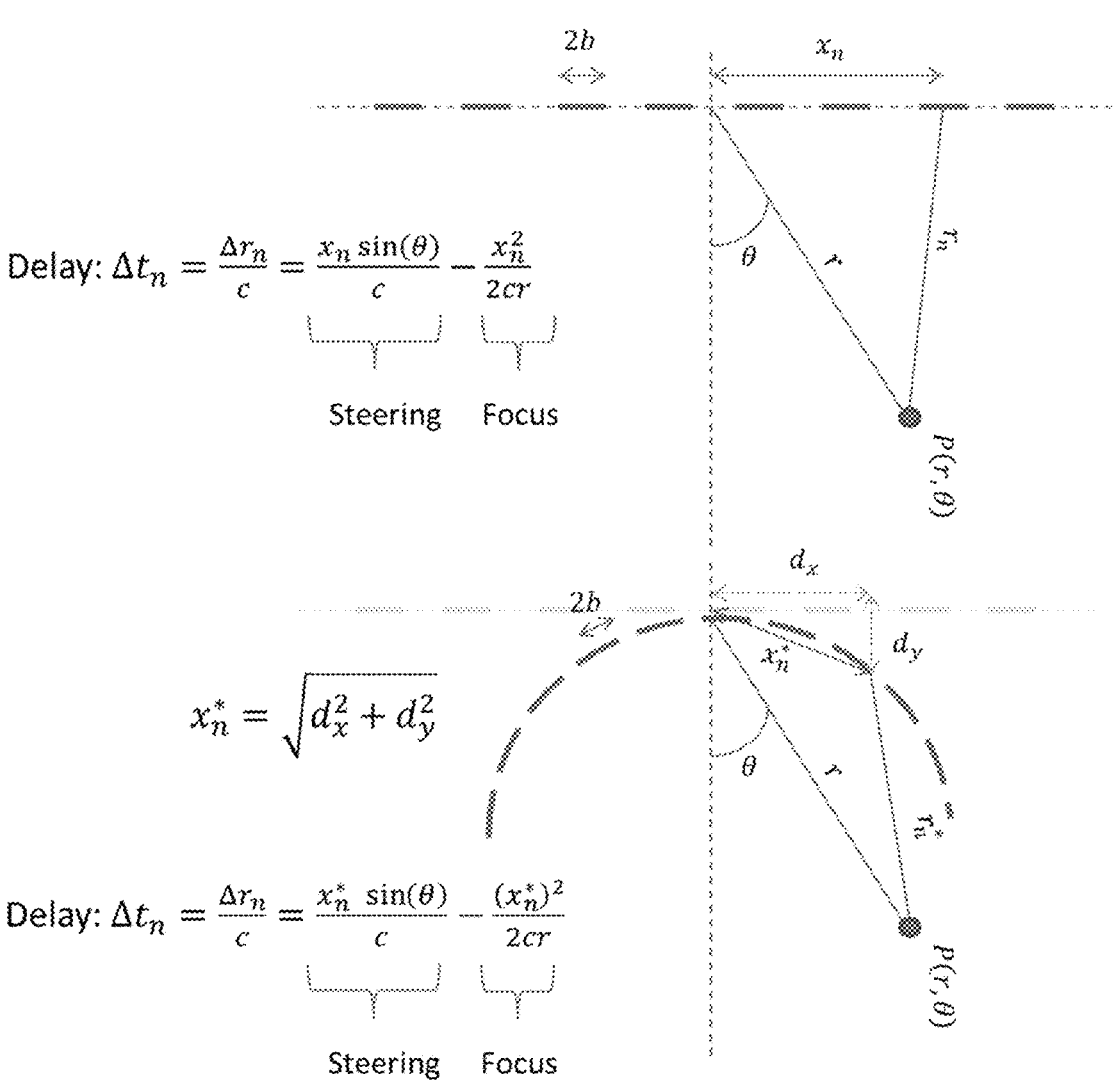
FIG. 5A is an exemplary diagram illustrating an alteration of phasing for a curved array according to an exemplary embodiment of the present disclosure.
FIG. 5B is an exemplary diagram illustrating exemplary modifications for elements for arbitrary coordinates in a curved array according to an exemplary embodiment of the present disclosure.

As the array can take on any shape within, for example, the 2 cm radius of curvature, it can be beneficial to adjust the phasing of each element appropriately. Traditionally, the elements of a phased array can be excited with delays proportional to the center of the array. When the array flexes to conform to a human body, these linear distances between the focus and the array center may no longer be accurate and can be adjusted. These can be accounted for geometrically as shown in FIGS. 5A and 5B. In particular, FIGS. 5A and 5B illustrate that the delay of any particular element, $\Delta t_n$, can be expressed in terms of distance moved from the original location an element was located from the reference point at the center of the array, $\Delta x_n^*$. The simulated results of accounting for, or failing to account for, the 2 cm radius of curvature of the described array are shown in FIGS. 6A and 6B. In particular, FIG. 6A shows an exemplary diagram illustrating simulation results showing the effect of a 2 cm radius of curvature on a 16×16 element array using curvature adjusted phasing, and FIG. 6B shows an exemplary diagram illustrating simulation results showing the effect of a 2 cm radius of curvature on a 16×16 element array using standard phasing according to an exemplary embodiment of the present disclosure. An array of test points can be simulated to be 5 mm apart, spaced from 10 mm to 55 mm in the z direction. The array was focused at 3 cm. If a traditional phasing paradigm can be used (e.g., without accounting for curvature), it can be difficult to distinguish individual point sources from one another.

FIG. 7 shows an exemplary flow diagram of a method 700 for generating an image of an anatomical structure according to an exemplary embodiment of the present disclosure. For example, at procedure 705, first information related to a shape of a flexible substrate having a plurality of ultrasound transducers can be received. At procedure 710, a phase for each of the ultrasound transducers can be controlled. At procedure 715, the ultrasound transducers can be activated with a phase determined, at least in part, by the shape of the flexible substrate and a focused ultrasound signal can be provided to the anatomical structure. At procedure 720, second information related to a return ultrasound signal from the anatomical structure that is based on the ultrasound signal can be received. At procedure 725, the image can be generated based on the return ultrasound signal.

Figure 8:
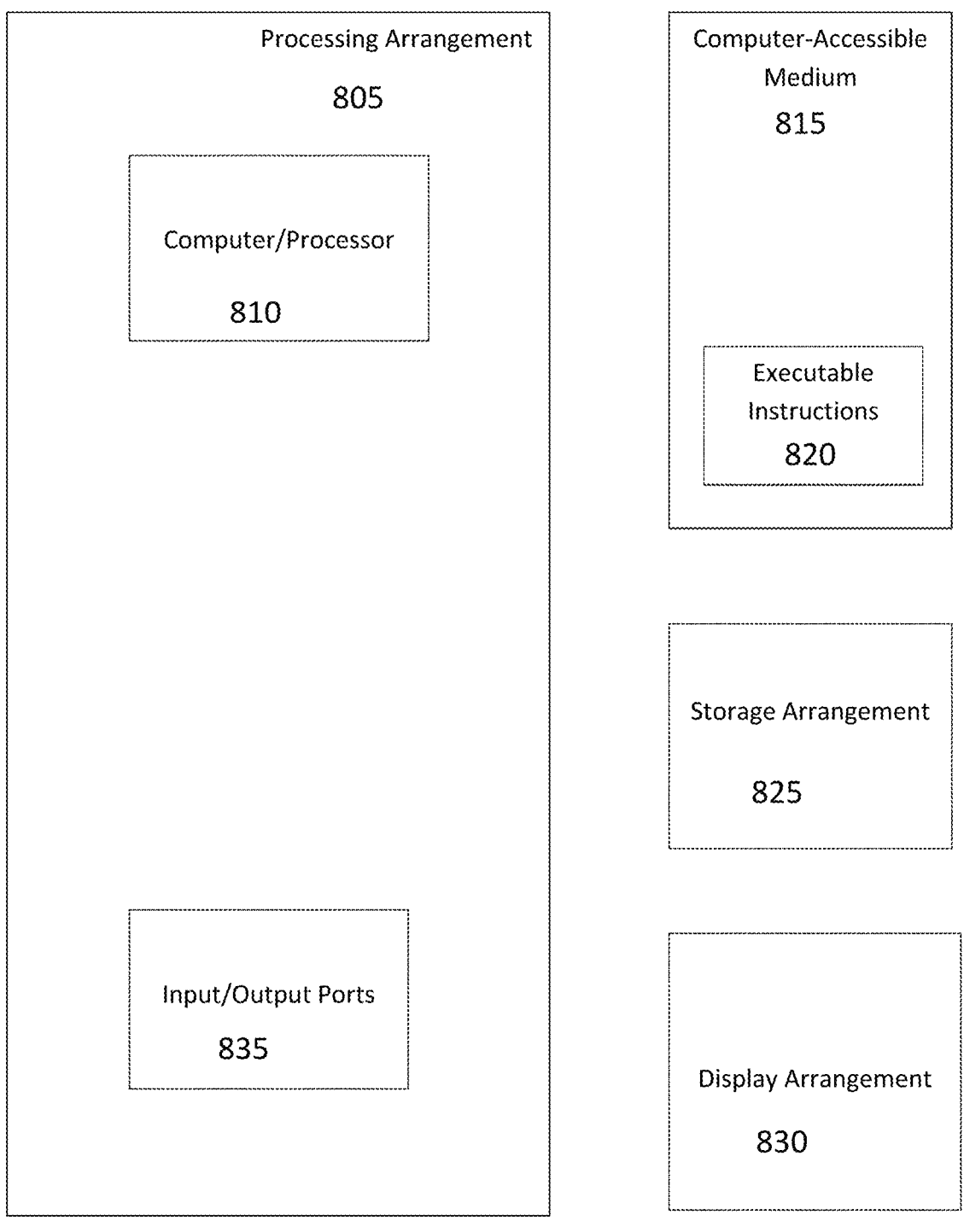
FIG. 8 is an illustration of an exemplary block diagram of an exemplary system in accordance with certain exemplary embodiments of the present disclosure.

FIG. 8 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 805. Such processing/computing arrangement 805 can be, for example entirely or a part of, or include, but not limited to, a computer/processor 810 that can include, for example one or more microprocessors, and use instructions stored on a computer-accessible medium (e.g., RAM, ROM, hard drive, or other storage device).

As shown in FIG. 8, for example a computer-accessible medium 815 (e.g., as described herein above, a storage device such as a hard disk, floppy disk, memory stick, CD-ROM, RAM, ROM, etc., or a collection thereof) can be provided (e.g., in communication with the processing arrangement 805). The computer-accessible medium 815 can contain executable instructions 820 thereon. In addition or alternatively, a storage arrangement 825 can be provided separately from the computer-accessible medium 815, which can provide the instructions to the processing arrangement 805 so as to configure the processing arrangement to execute certain exemplary procedures, processes, and methods, as described herein above, for example.

Further, the exemplary processing arrangement 805 can be provided with or include an input/output ports 835, which can include, for example a wired network, a wireless network, the internet, an intranet, a data collection probe, a sensor, etc. As shown in FIG. 8, the exemplary processing arrangement 805 can be in communication with an exemplary display arrangement 830, which, according to certain exemplary embodiments of the present disclosure, can be a touch-screen configured for inputting information to the processing arrangement in addition to outputting information from the processing arrangement, for example. Further, the exemplary display arrangement 830 and/or a storage arrangement 825 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. An ultrasound apparatus, comprising:
a flexible substrate;
a plurality of ultrasound transducers coupled to the flexible substrate; and
at least one integrated circuit (IC) mounted on the substrate and configured to drive and control the ultrasound transducers, wherein the at least one IC is configured to control an excitation phase of the ultrasound transducers based at least in part on a shape or a dimension of the flexible substrate, and wherein the at least one IC includes an array of at least some of the ultrasound transducers which are configured to receive and transmit ultrasound energy,
wherein:
the plurality of ultrasound transducers include (i) at least one first transducer array, and (ii) at least one second transducer array,
the at least one IC includes (i) at least one first slave IC, (ii) at least one second slave IC, and (iii) at least one master IC,
the at least one first transducer array is mounted on the at least one first slave IC,
the at least one second transducer array is mounted on the at least one second slave IC, and the at least one first slave IC and the at least one second slave IC are controlled by the at least one master IC, and
wherein the at least one master IC is provided separately and at a distance from the plurality of ultrasound transducers.

2. The ultrasound apparatus of claim 1, wherein the at least one IC includes at least two ICs, wherein a first IC of the at least two ICs is configured to drive and control the ultrasound transducers, and wherein a second IC of the at least two ICs is configured to control the first IC.

3. The ultrasound apparatus of claim 1, wherein the ultrasound transducers are an array of bulk piezoelectric transducers.

4. The ultrasound apparatus of claim 1, wherein the substrate is a flexible printed circuit board.

5. The ultrasound apparatus of claim 1, wherein the at least one IC is configured to separately control (i) a transmission of ultrasound energy from each of the transducers, (ii) a magnitude and (iii) a phase, wherein the at least one IC is configured to use the phase to focus the transmitted energy compensating for a curvature of the ultrasound apparatus.

6. The ultrasound apparatus of claim 1, wherein the array of at least some of the ultrasound transducers elements of the at least one IC is configured to receive and detect back-reflected ultrasound energy from one or more others of the ultrasound transducers to form an image.

7. The ultrasound apparatus of claim 1, wherein the at least one IC includes a plurality of ICs, and wherein each of the ICs is configured to control a phase of a subset of the ultrasound transducers.

8. The ultrasound apparatus of claim 1, wherein the at least one IC is a complementary-metal-oxide-semiconductor (CMOS) chip.

9. The ultrasound apparatus of claim 8, wherein the at least one IC is a thinned and flexible CMOS chip.

10. The ultrasound apparatus of claim 9, wherein the ultrasound transducers are mounted on the thinned and flexible CMOS chip.

11. The ultrasound apparatus of claim 1, wherein (i) the at least one first slave IC controls the excitation phase of each transducer in the at least one first transducer array, and (ii) the at least one second slave IC controls the excitation phase of each transducer in the at least one second transducer array.

12. The ultrasound apparatus of claim 1, wherein the plurality of transducers comprises a first transducer array and the second transducer array, and further comprising at least one computer arrangement configured to:
receive ultrasound imaging information from at least one of the first transducer array or the second transducer array; and
generate at least one image based on the ultrasound imaging information.

13. The ultrasound apparatus of claim 1, wherein the ultrasound apparatus is configured to be attached to at least one patient.

14. The ultrasound apparatus of claim 1, wherein the at least one IC includes a plurality of ICs, each of which includes a subset of the ultrasound transducers.

15. An ultrasound apparatus, comprising:
a flexible printed circuit board (PCB);
a plurality of slave complementary-metal-oxide-semiconductor (CMOS) chips disposed on the flexible PCB;
a plurality of ultrasound transducer arrays, wherein each of the ultrasound transducer arrays is mounted on, and controlled by, at least one of the slave CMOS chips; and at least one master CMOS chip configured to control excitation phases of the slave CMOS chips based at least in part on a shape or a dimension of the flexible PCB, wherein:

the plurality of ultrasound transducer arrays includes (i) at least one first transducer array, and (ii) at least one second transducer array, the slave CMOS chips include (i) at least one first slave integrated chip (IC), and (ii) at least one second slave IC, the at least one first transducer array is mounted on the at least one first slave IC, the at least one second transducer array is mounted on the at least one second slave IC, and the at least one first slave IC and the at least one second slave IC are controlled by the at least one master CMOS chip, and wherein the at least one master CMOS chip is provided separately and at a distance from the plurality of ultrasound transducer arrays.

16. The ultrasound apparatus of claim 15, wherein the slave CMOS chips are thinned and flexible slave CMOS chips and the at least one master CMOS chip is at least one thinned and flexible master CMOS chip.

17. The ultrasound apparatus of claim 15, wherein the ultrasound transducer arrays include a plurality of piezo-electric transducers.

18. The ultrasound apparatus of claim 15, further comprising at least one computer arrangement configured to:

receive ultrasound imaging information from the at least one master CMOS chip; and generate at least one image based on the ultrasound imaging information.

19. The ultrasound apparatus of claim 15, wherein the ultrasound apparatus is configured to be attached to at least one patient.

20. The ultrasound apparatus of claim 15, wherein one or more of the plurality of slave CMOS chips includes at least one IC that has the array of at least some of the ultrasound transducers arrays which are configured to receive and transmit the ultrasound energy.

21. The ultrasound apparatus of claim 20, wherein the at least one IC includes a plurality of ICs, each of which includes a subset of the ultrasound transducers arrays.

22. An ultrasound apparatus, comprising:

a flexible substrate;

a plurality of ultrasound transducers mounted to the flexible substrate; and at least one integrated circuit (IC) mounted on the substrate to drive and control the ultrasound transducers, wherein the at least one IC is a complementary-metal-oxide-semiconductor (CMOS) chip, wherein the at least one IC is a thinned and flexible CMOS chip, wherein the at least one IC is configured to control an excitation phase of the ultrasound transducers based at least in part on a shape or a dimension of the flexible substrate, wherein the at least one IC includes an array of at least some of the ultrasound transducers which are configured to receive and transmit ultrasound energy, wherein the ultrasound transducers are mounted on the thinned and flexible CMOS chip, wherein:

the plurality of ultrasound transducers include (i) at least one first transducer array, and (ii) at least one second transducer array, the at least one IC includes (i) at least one first slave IC, (ii) at least one second slave IC, and (iii) at least one master IC, the at least one first transducer array is mounted on the at least one first slave IC, the at least one second transducer array is mounted on the at least one second slave IC, and the at least one first slave IC and the at least one second slave IC are controlled by the at least one master IC, and wherein the at least one master IC is provided separately and at a distance from the plurality of ultrasound transducers.

23. The ultrasound apparatus of claim 22, wherein the at least one IC includes a plurality of ICs, each of which includes a subset of the ultrasound transducers.

* * * * *